United States Patent
Boskamp (10) Patent No.: US 9,116,215 B2
(45) Date of Patent: Aug. 25, 2015

(54) COMPOSITE RF SHIELD AND METHOD OF MAKING SAME

(71) Applicant: General Electric Company, Schenectady, NY (US)

(72) Inventor: Eddy Benjamin Boskamp, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 145 days.

(21) Appl. No.: 13/737,458

(22) Filed: Jan. 9, 2013

(65) Prior Publication Data

US 2014/0194727 A1   Jul. 10, 2014

(51) Int. Cl.
| | |
|---|---|
| *G01R 33/422* | (2006.01) |
| *A61B 5/00* | (2006.01) |
| *G01R 33/00* | (2006.01) |
| *G01R 33/48* | (2006.01) |
| *A61B 5/055* | (2006.01) |
| *G01R 33/025* | (2006.01) |
| *G01T 1/16* | (2006.01) |
| *H05K 9/00* | (2006.01) |

(52) U.S. Cl.
CPC ............ *G01R 33/422* (2013.01); *A61B 5/0035* (2013.01); *A61B 5/055* (2013.01); *G01R 33/0052* (2013.01); *G01R 33/0076* (2013.01); *G01R 33/025* (2013.01); *G01R 33/481* (2013.01); *G01T 1/1603* (2013.01); *A61B 2562/182* (2013.01); *H05K 9/0081* (2013.01); *Y10T 29/49016* (2015.01)

(58) Field of Classification Search
USPC .................................................. 250/363.05
See application file for complete search history.

(56) References Cited

U.S. PATENT DOCUMENTS

| | | | | |
|---|---|---|---|---|
| 5,367,261 | A * | 11/1994 | Frederick ...................... | 324/318 |
| 6,522,144 | B2 | 2/2003 | Boskamp | |
| 6,885,194 | B2 | 4/2005 | Boskamp | |
| 7,109,712 | B2 | 9/2006 | Boskamp | |
| 7,667,457 | B2 * | 2/2010 | Linz et al. ..................... | 324/318 |
| 2009/0221903 | A1 * | 9/2009 | Corbeil et al. ................ | 600/411 |

FOREIGN PATENT DOCUMENTS

WO    WO 2012/025860 A1 *   3/2012   ................... 342/322

* cited by examiner

*Primary Examiner* — Unsu Jung
*Assistant Examiner* — Phong K Huynh
(74) *Attorney, Agent, or Firm* — Ziolkowski Patent Solutions Group, SC (57) ABSTRACT

An imaging apparatus comprises an RF coil former comprising an inner surface and an outer surface and a composite RF shield positioned adjacently to the outer surface of the RF coil former so as to be formed about the RF coil former. The MRI system also comprises an RF coil positioned on the inner surface of the RF coil former. The RF coil former comprises a generally cylindrical member having an indented portion indented in a radial direction inwardly from the outer surface, and the composite RF shield comprises a first shield material positioned about the outer surface of the RF coil former, a second shield material position about the indented portion of the RF coil former, and a conformal shield material positioned about the RF coil former that electrically couples the first shield material to the second shield material.

19 Claims, 6 Drawing Sheets

COMPOSITE RF SHIELD AND METHOD OF MAKING SAME

BACKGROUND OF THE INVENTION

Embodiments of the invention relate generally to magnetic resonance (MR) imaging, and more specifically, to an RF shield of an RF coil assembly configured to accommodate positioning of elements therein, such as a positron emission tomography (PET) detector array for use in a hybrid PET-MRI system.

PET imaging involves the creation of tomographic images of positron emitting radionuclides in a subject of interest. A radionuclide-labeled agent is administered to a subject positioned within a detector ring. As the radionuclides decay, positively charged particles known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV.

It is these gamma rays that are detected by the scintillators of the detector ring. When struck by a gamma ray, each scintillator illuminates, activating a photovoltaic component, such as a photodiode. The signals from the photovoltaics are processed as incidences of gamma rays. When two gamma rays strike oppositely positioned scintillators at approximately the same time, a coincidence is registered. Data sorting units process the coincidences to determine which are true coincidence events and sort out data representing deadtimes and single gamma ray detections. The coincidence events are binned and integrated to form frames of PET data which may be reconstructed into images depicting the distribution of the radionuclide-labeled agent and/or metabolites thereof in the subject.

MR imaging involves the use of magnetic fields and excitation pulses to detect the free induction decay of nuclei having net spins. When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a RF magnetic field (excitation field $B_1$) which is in the x-y plane, i.e. perpendicular to the DC magnetic field (B0) direction, and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well-known reconstruction techniques.

In combination PET-MRI systems, the PET detector array needs to be placed outside the RF shield associated with the MRI scanner, in order to shield the sensitive detector array from the high amplitude RF fields of the MRI scanner. As set forth in U.S. patent application Ser. No. 13/461,985, filed May 2, 2012 by General Electric Company, in a combined PET-MRI scanner, the RF shield and RF coil former may be constructed with an indented portion to allow space for a PET detector array to be positioned therein. The RF shield and RF coil former have a stepped configuration to allow for the indented portion to be formed in the center of the RF shield.

As further set forth in U.S. patent application Ser. No. 13/461,985, a typical RF shield may be made from a stainless steel mesh material configured to conform to the stepped configuration of the RF coil former. The steps of the RF coil former are cylindrical but have different diameters. Thus, the indented portion usually has the smallest diameter, while the portions of the RF coil former farthest from the indented portion usually have the largest diameter. A series of steps leading from the largest diameter to the smallest diameter may be formed in the RF coil former to accommodate the PET detector as desired.

The RF shield, when constructed of stainless steel mesh, is typically formed with multiples pieces of overlapping mesh such that separate pieces can conform to the steps of different diameters. To join the multiple pieces together to form a single RF shield, the overlapping edges of the separate pieces are cut to allow overlapping portions to extend toward the adjacent step. The overlapping portions extending toward each other from the different steps are soldered together to allow RF conductivity between the adjacent steps. In this manner, the RF shield for the RF coil former may be constructed to conform to the various steps in the RF coil former. Constructing the RF shield in this manner, however, is typically very costly due to the labor intensive work needed to form the RF shield.

It would therefore be desirable to provide an RF shield and manufacturing process for a stepped RF coil former of a combined PET-MRI scanner that overcome the aforementioned drawbacks.

BRIEF DESCRIPTION OF THE INVENTION

Embodiments of the invention provide an RF coil assembly and composite RF shield for use in a stand-alone or hybrid MRI system.

According to one aspect of the invention, an imaging apparatus comprises a magnetic resonance imaging (MRI) system comprising a plurality of gradient coils positioned about a patient bore, an RF coil former comprising an inner surface and an outer surface, and a composite RF shield positioned adjacently to the outer surface of the RF coil former so as to be formed about the RF coil former. The MRI system also comprises an RF coil positioned on the inner surface of the RF coil former and about the patient bore, with the RF coil coupled to a pulse generator to emit an RF pulse sequence and receive resulting MR signals from a subject of interest. The RF coil former comprises a generally cylindrical member having an indented portion indented in a radial direction inwardly from the outer surface, and the composite RF shield comprises a first shield material positioned about the outer surface of the RF coil former, a second shield material positioned about the indented portion of the RF coil former, and a conformal shield material positioned about the RF coil former that electrically couples the first shield material to the second shield material.

According to another aspect of the invention, a PET-MRI apparatus comprises a magnetic resonance imaging (MRI) system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest. The PET-MRI apparatus also comprises a positron emission tomography (PET) system having a detector array positioned to encircle the bore, with the detector array being controlled to acquire PET emissions of the subject of interest. The RF shield comprises a first RF shield portion forming a raised portion, a second RF shield portion forming an indented portion, the indented portion being indented from the raised portion in the radial direction inwardly toward the patient bore, and a conformal shield portion coupling the first RF shield portion to the second RF shield portion.

According to yet another aspect of the invention, a method of forming a composite RF shield comprises positioning a first shield material about an outer surface of an RF coil former and positioning a second shield material about an indented portion of the RF coil former, wherein the indented portion indented in a radial direction inwardly from the outer surface. The method also comprises applying a conformal shield material about the RF coil former to electrically couple the first shield material to the second shield material.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

An RF coil assembly is provided that includes an RF shield having an indentation formed therein in a region thereof. An RF coil in the RF coil assembly is shaped to conform to the shape of the RF shield so as to increase the efficiency of the RF coil and reduce the local specific absorption rate (SAR) experienced by a patient.

According to embodiments of the invention, the RF coil assembly can be implemented in a variety of imaging systems or apparatuses. For example, the RF coil assembly can be incorporated into a stand-alone MR imaging system or can be incorporated into a hybrid MR imaging system, such as a hybrid PET-MR imaging system, for example. Thus, while embodiments of the invention are set forth here below with respect to a hybrid PET-MR imaging system, it is recognized that other stand-alone and hybrid MR imaging systems are considered to be within the scope of the invention.

Figure 1:
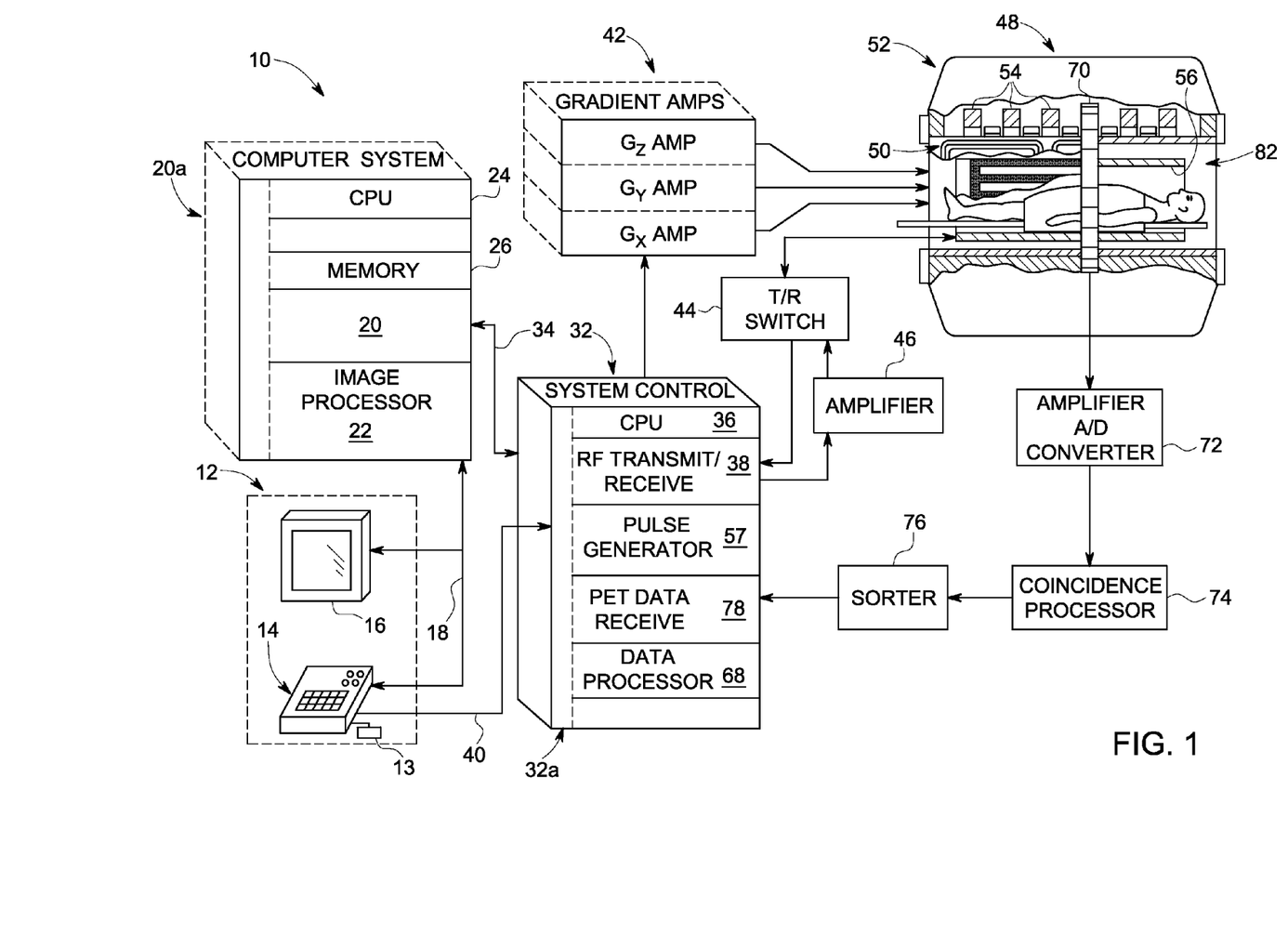
FIG. 1 is a schematic block diagram of an exemplary PET-MR imaging system for use with an embodiment of the invention.

Referring to FIG. 1, the major components of an exemplary hybrid PET-MR imaging system 10 that may incorporate embodiments of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules, such as an image processor module 22, a CPU module 24 and a memory module 26. The computer system 20 may also be connected to permanent or back-up memory storage, a network, or may communicate with a separate system control 32 through link 34. The input device 13 can include a mouse, keyboard, track ball, touch activated screen, light wand, or any similar or equivalent input device, and may be used for interactive geometry prescription.

The system control 32 includes a set of modules in communication with one another and connected to the operator console 12 through link 40. It is through link 34 that the system control 32 receives commands to indicate the scan sequence or sequences that are to be performed. For MR data acquisition, an RF transmit/receive module 38 commands the scanner 48 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 44 and amplifier 46 control the flow of data to scanner 48 from RF transmit module 38 and from scanner 48 to RF receive module 38. The system control 32 also connects to a set of gradient amplifiers 42, to indicate the timing and shape of the gradient pulses that are produced during the scan.

The gradient waveform instructions produced by system control 32 are sent to the gradient amplifier system 42 having Gx, Gy, and Gz amplifiers. Amplifiers 42 may be external of scanner 48 or system control 32, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil 56 (i.e., whole-body RF coil). Alternatively, the gradient coils of gradient coil assembly 50 may be independent of the magnet assembly 52. The coils 56 of the RF coil may be configured for both transmitting and receiving, or for transmit-only or receive-only. A pulse generator 57 may be integrated into system control 32 as shown, or may be integrated into scanner equipment 48, to produce pulse sequences or pulse sequence signals for the gradient amplifiers 42 and/or the RF coil 56. In addition, pulse generator 57 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 56 or by separate receive coils and are then transmitted to the RF transmit/receive module 38 via T/R switch 44. The MR signals are demodulated, filtered, and digitized in the data processing section 68 of the system control 32.

An MR scan is complete when one or more sets of raw k-space data has been acquired in the data processor 68. This raw k-space data is reconstructed in data processor 68 which operates to transform the data (through Fourier or other techniques) into image data. This image data is conveyed through link 34 to the computer system 20 where it is stored in memory 26. Alternatively, in some systems computer system 20 may assume the image data reconstruction and other functions of data processor 68. In response to commands received from the operator console 12, the image data stored in memory 26 may be archived in long term storage or may be further processed by the image processor 22 or CPU 24 and conveyed to the operator console 12 and presented on the display 16.

In combined MR-PET scanning systems, PET data may be acquired simultaneously with the MR data acquisition described above. Thus, scanner 48 also contains a positron emission detector array or ring 70, configured to detect gamma rays from positron annihilation radiations emitted from a subject. Detector array 70 preferably includes a plurality of scintillators and photovoltaics arranged about a gantry. Detector array 70 may, however, be of any suitable construction for acquiring PET data. In addition, the scintillator packs, photovoltaics, and other electronics of the detector array 70 are shielded from the magnetic fields and/or RF fields applied by the MR components 54, 56 by way of an RF shield (not shown), as will be explained in detail below.

Gamma ray incidences detected by detector array 70 are transformed, by the photovoltaics of the detector array 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 26 for subsequent processing 68. PET images may then be reconstructed by image processor 22 and may be combined with MR images to produce hybrid structural and metabolic or functional images. Conditioning circuits 72, coincidence processor 74 and sorter 76 may each be external of scanner 48 or system control 32, or may be integrated therein.

Figure 2:
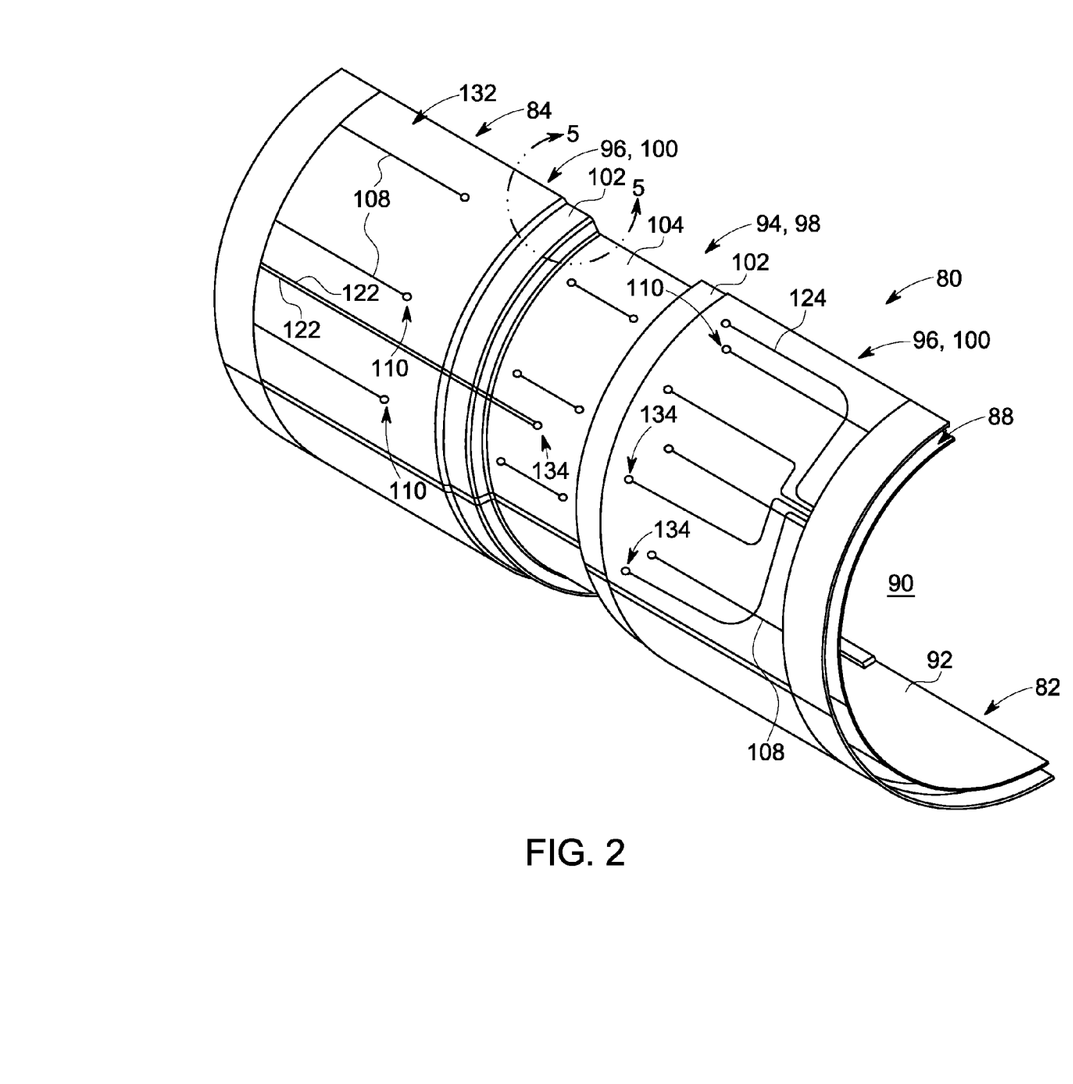
FIGS. 2 and 3 are perspective views of an RF coil assembly for use in the PET-MR imaging system of FIG. 1 according to an embodiment of the invention.
Figure 3:
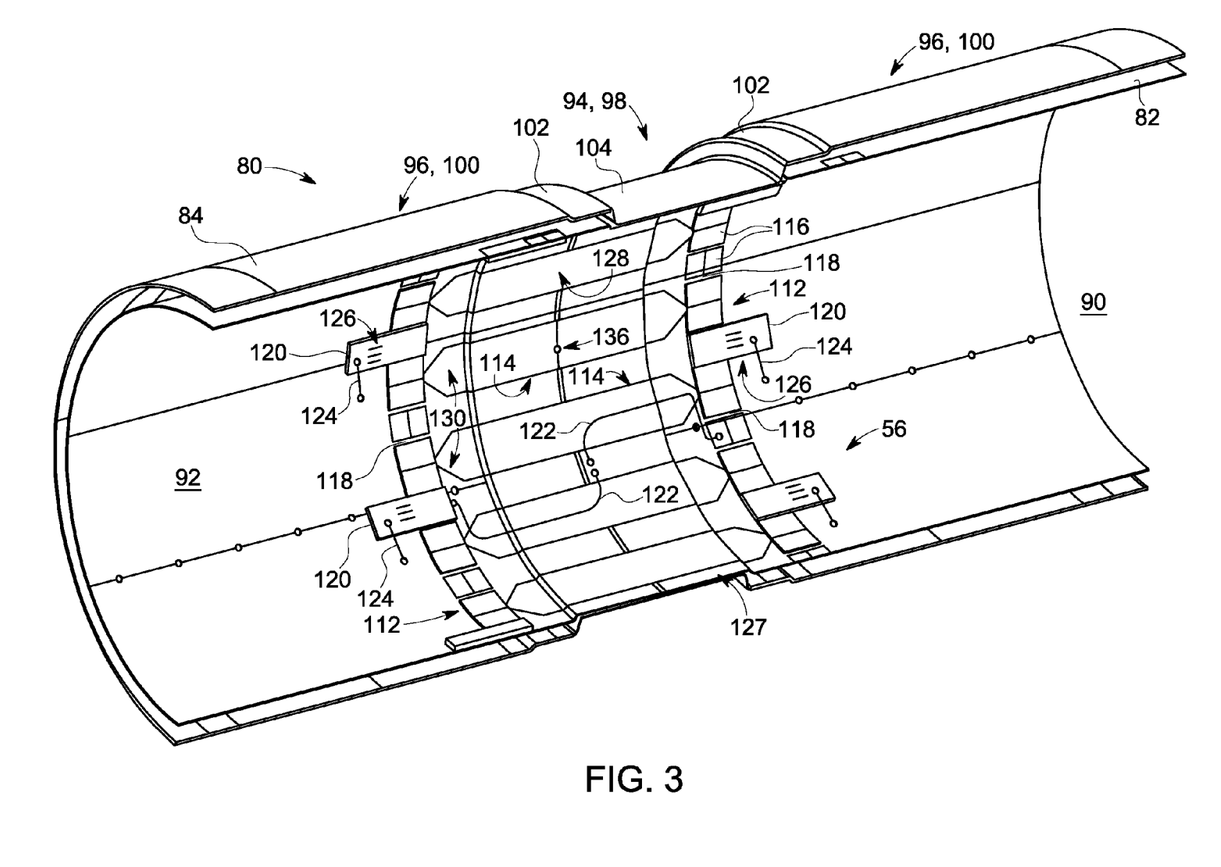

Referring now to FIGS. 2 and 3, an RF coil assembly 80 that is included in the hybrid PET-MR imaging system 10 is shown, although it is recognized that RF coil assembly 80 could also be implemented for use in other stand-alone MRI systems or other hybrid MRI systems. The RF coil assembly 80 includes an RF coil former or tube 82, an RF shield 84, and the RF body coil 56. According to an embodiment of the invention, the RF shield 84 is formed of multiple materials such as stainless steel mesh and a conformable metal material configured to conductively join separate mesh sections together as described below. The RF coil former 82, according to an embodiment, is formed of fiberglass or fiber reinforced plastic (FRP) cylinders on the radially inner and radially outer surfaces, with a foam material sandwiched between the inner and outer surfaces, although it is recognized that other suitable materials could also be used. The RF shield 84 is positioned on the outer surface 88 of RF coil former 82 and is formed there about. The RF coil 56 is formed on an inner surface 92 of RF coil former 82 with an annular receiving or imaging area 90 (i.e., patient bore), and is separated radially from gradient coils 50 by RF shield 84, with the RF shield 84 functioning to de-couple the RF coils 56 from the gradient coils 50 (FIG. 1) in the PET-MR imaging system 10.

As shown in FIG. 2, the RF coil former 82 is generally cylindrical in shape but includes an indentation or indented portion 94 formed therein in a radial direction and in an area that corresponds to the PET detector array 70 (FIG. 1) of the PET-MR imaging system 10. Thus, the indented portion 94 will be formed in a generally central area lengthwise on the RF coil former 82, with a pair of raised or stepped-up portions 96 of the RF coil former 82 being formed on opposing sides of the indented portion 94 and at opposing ends of the RF coil former 82. The RF shield 84 is applied over the outer surface 88 of RF coil former 82 and conforms to the RF coil former 82, such that the RF shield 84 has an identical shape as the outer surface 88 of the RF coil former 82. The RF shield 84 thus also includes an indentation/indented portion 98 formed therein in the area that corresponds to the PET detector array 70 (FIG. 1), with the indented portion 98 being between raised portions 100 of the RF shield 84.

Figure 4:
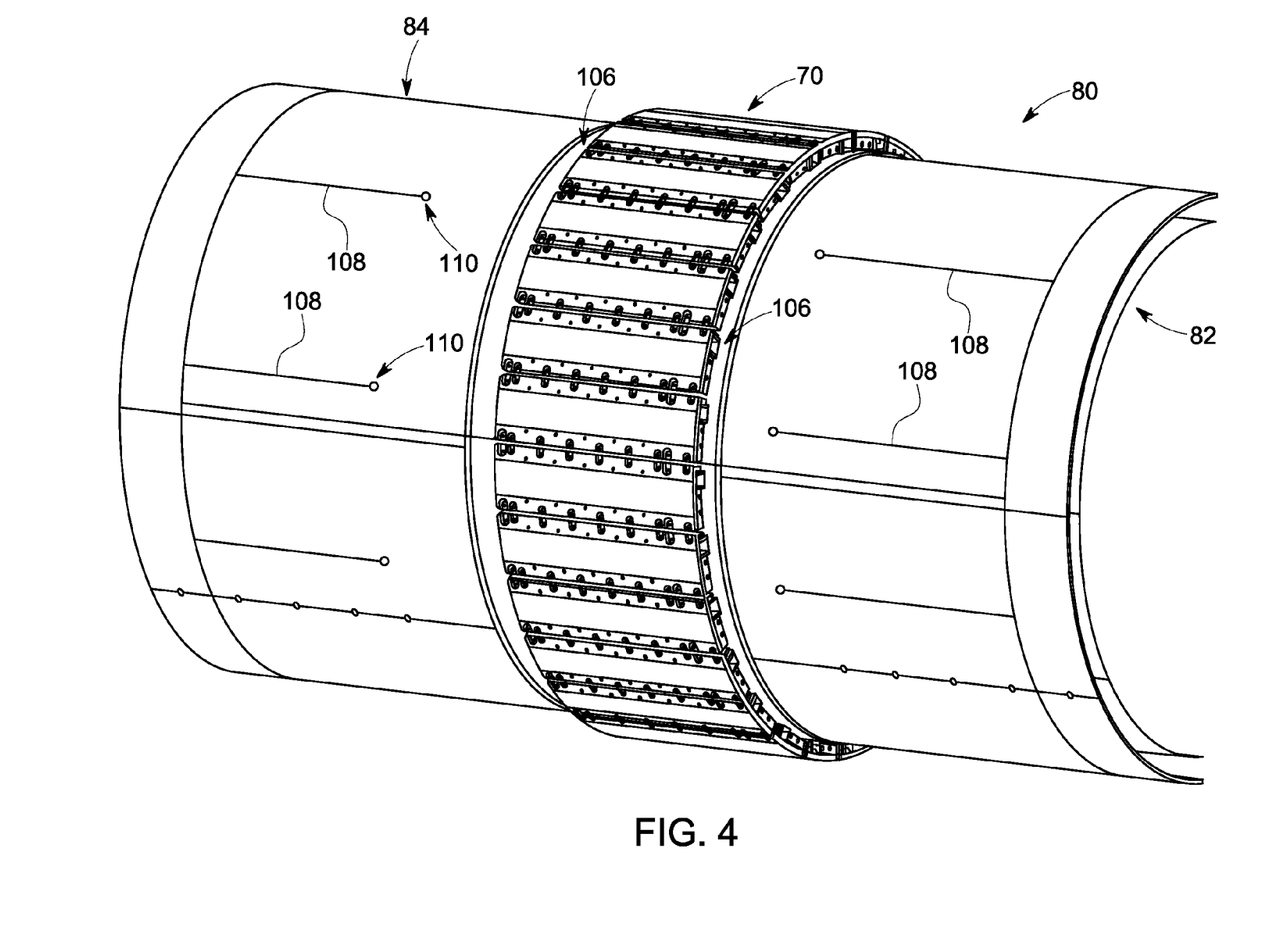
FIG. 4 is a perspective view of the RF coil assembly of FIGS. 2 and 3 with a PET detector array positioned on the RF shield according to an embodiment of the invention.

According to an exemplary embodiment of the invention, the indented portions 94, 98 in RF coil former 82 and RF shield 84 have a stepped configuration. As shown in FIG. 2, a first step 102 and a second step 104 are formed in the indented portions 94, 98 of RF coil former 82 and RF shield 84, with the second step 104 being further indented from raised portions 96, 100 of the RF coil former 82 and RF shield 84 than the first step 102. The first and second steps 102, 104 accommodate positioning of the detector array 70 and an accompanying mechanical support frame 106 therein, as shown in FIG. 4. That is, mechanical support frame 106 can be positioned on first step 102 of the indented portions 94, 98, such that an outer surface of the support frame is flush with the raised portions 100 of the RF shield 84. Similarly, detector array 70 may be positioned on second step 104 of the indented portions 94, 98, such that the detector array is flush with the raised portions 100 of the RF shield 84.

As shown in FIG. 2, according to one embodiment of the invention, slits 108 are formed in RF shield 84 extending in the z-direction. The slits 108 may be formed to have a width of 1 mm, for example, and are configured to reduce heating caused by gradient field induced eddy currents in the RF shield 84 during operation of the PET-MR imaging system 10 by increasing impedance for the gradient eddy currents due to increased path length. The slits 108 are formed in an outer region of each of raised portions 100 of RF shield 84 and in the region of RF shield 84 that accommodates the detector array 70, i.e., in the region of second step 104. According to an exemplary embodiment, the end of each slit 108 has a bubble or circular opening 110 formed thereat, to reduce the local eddy current density, and hence local heat generation.

Referring now to FIG. 3, positioning of RF coil 56 on the inner surface 92 of RF coil former 82 is shown. The RF coil 56 is, in general, configured as a standard birdcage resonator that includes a pair of end rings 112 and a plurality of rungs 114 extending between the end rings 112. Each of end rings 112 is composed of a plurality of segments 116, with capacitors 118 being positioned between the segments 116. Decoupling networks or boards 120 are also positioned on end rings 112 of RF coil 56 to decouple the RF coil 56 from other coils in the bore. RF cables 122 and DC power cables 124 provide power to RF coil 56 and decoupling boards 120 respectively, with chokes 126 on the decoupling boards 120 functioning to separate the RF circuit from the DC circuit.

As shown in FIG. 3, according to an exemplary embodiment of the invention, the RF coil 56 is formed so as to generally conform to a shape of the inner surface 92 of RF coil former 82. That is, a portion 127 of the inner surface 92 of the RF coil former 82 is indented in a radial direction inwardly in an area corresponding to the indented portion 94 on the outer surface 88 of the RF coil former 82. Accordingly, the rungs 114 are not straight but have a stepped configuration. A center area 128 of each of the rungs 114 is stepped-down so as to be closer to the patient space/imaging area 90 in the area corresponding to the indented portion 127. Portions 130 of the rungs 114 are then stepped-up and further away from the patient space/imaging area 90 as they approach the end rings 112, in the areas corresponding to the raised portions 96 on the RF coil former 82. The end ring capacitors 118 and the E-fields associated with the end rings 112 are thus further from the patient, thereby reducing local specific absorption rate (SAR), which is related to patient heating.

As further shown in FIG. 3, the construction of RF shield 84 and RF coil former 82 is such that, in the indented portions 94, 98 of the RF coil former 82 and RF shield 84, the RF shield 84 gets radially close to the rungs 114 of the RF coil 56 (i.e., much closer to the rungs 114 of the RF coil 56 than in a conventional birdcage resonator) due to a depth of indented portions 94, 98 extending inwardly, thereby slightly diminishing the efficiency of the RF coil 56. To increase the efficiency of the RF coil 56, the radial distance between the end rings 112 of the RF coil 56 and the RF shield 84 is increased as compared to the distance between the rungs 114 and the RF shield 84—and is much larger than in a conventional birdcage.

Also shown in FIGS. 2 and 3 is the placement of the RF cables 122 and DC cables 124 in RF coil assembly 80 that provide power to the RF coil 56 and the decoupling networks 120, respectively. According to an exemplary embodiment of the invention, the RF and DC cables 122, 124 are routed almost entirely along an outer surface 132 of RF shield 84 in order to prevent a high E-field from inducing a large common mode current on the shields of the respective cables. Holes 134 are formed in RF shield 84 and RF coil former 82 to provide for routing of the cables 122, 124 to the inner surface 92 of RF coil former 82, such that the cables 122, 124 can be connected to RF coil 56 and decoupling networks 120.

With respect to the RF cables 122, as shown in FIG. 3, it is seen that the cables 122 are soldered to rungs 114 of RF coil 56 at a location that corresponds to a center point 136 (in the z-direction) of the rungs 114, before the cables 122 are routed along the rungs 114 to each of the end rings 112 of RF coil 56. The E-field at the center 136 of rungs 114 is approximately zero, and thus soldering of the outer shield/housing of the RF cable 122 to the RF coil 56 at this location is a further method to prevent RF cable 122 from being sensitive to transmit E-field induced currents on its shield. The routing of the RF cables 122 in the manner shown in FIGS. 2 and 3 thus provides for proper and efficient operation of RF coil 56.

Figure 5:
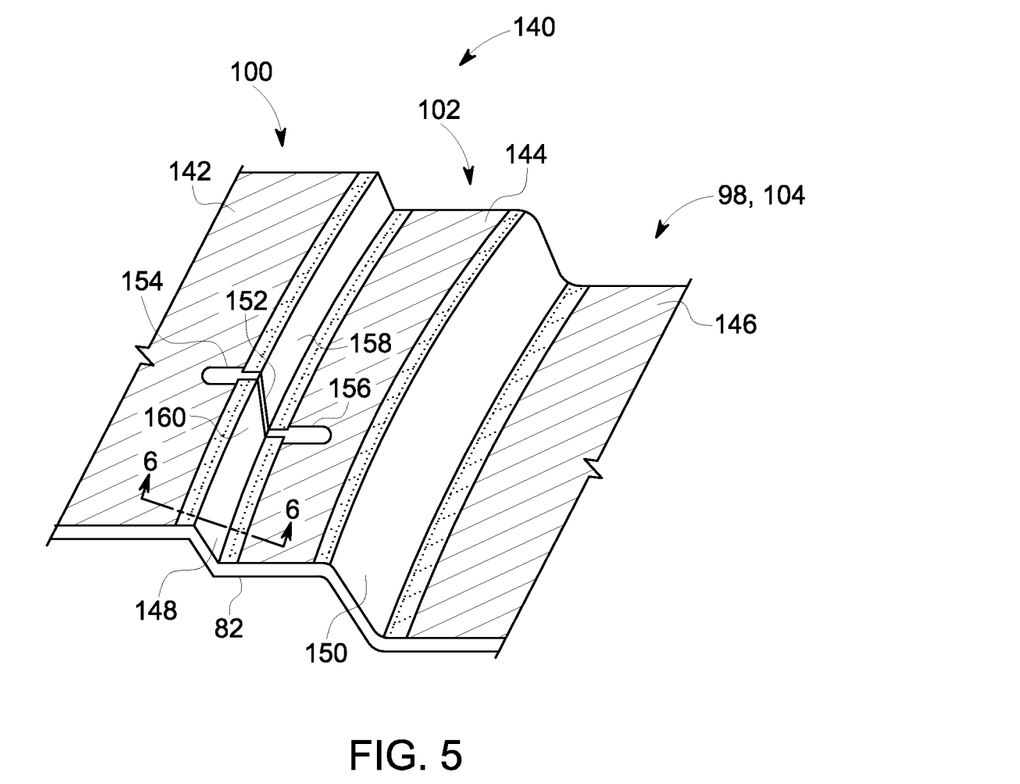
FIG. 5 is an isometric view of a composite RF shield taken along line 5-5 of FIG. 2 according to an embodiment of the invention.

FIG. 5 illustrates an isometric view of a composite, multi-material RF shield 140 taken along line 5-5 of FIG. 2 according to an embodiment of the invention. RF shield 140 is formed by positioning a plurality of sheets 142, 144, 146 of the first material about the circumference of RF coil former 82. For example, first material sheet 142 is positioned about the circumference of raised portion 100 of former 82, second material sheet 144 is positioned about the circumference of first step 102, and third material sheet 146 is positioned about the circumference of second step 104. In one embodiment, sheets 142-146 may be substantially rectangular sheets positioned about former 82 to form RF shield cylinders. In addition, sheets 142-146 are prepared so as to conform to the cylindrical section over which they are placed. That is, sheets 142-146 do not overlap themselves but are joined together using a separate material.

To join sheets 142-146 together to form a single RF shield about former 82, a pair of conformal shields 148, 150 are applied to electrically join sheet 142 to 144 and to join sheet 144 to 146 to form a composite RF shield. According to one embodiment, conformal shields 148, 150 may be a conductive paint or polymer painted or sprayed on former 82 so as to overlap the adjoining sheets 142-146. The conductive paint may be, for example, copper, silver, or other collectively conductive paint configured to electrically join adjacent sheets 142-146.

Figure 6:
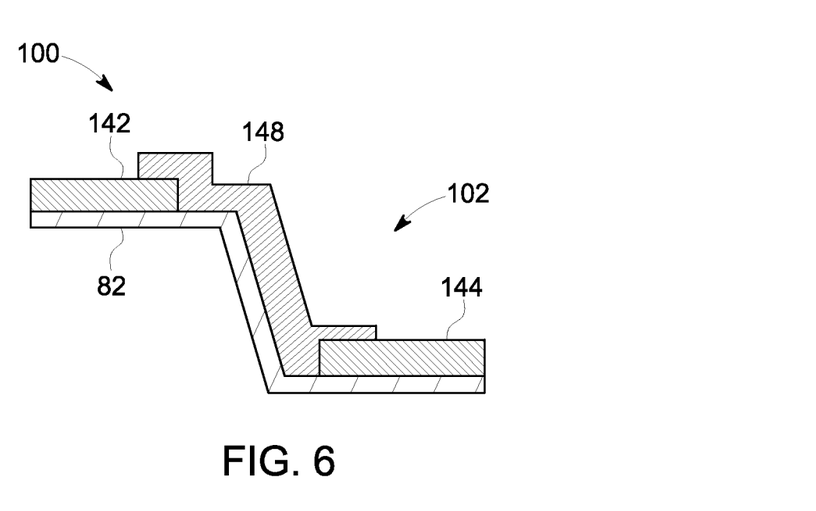
FIG. 6 is a cross-sectional view of a former and RF shield assembly taken a long line 6-6 of FIG. 5 according to an embodiment of the invention.

Referring to FIG. 6, a cross-sectional view of former 82 and RF shield 140 taken along line 6-6 of FIG. 5 is shown according to an embodiment of the invention. As illustrated, sheets 142, 144 of an RF conductive material are showing positioned about RF coil former 82. To electrically couple sheets 142, 144 as described above, conformal shield 148 is applied so as to overlap sheet 142 on raised portion 100 and so as to overlap sheet 144 on first step 102. Accordingly, sheet 142 is electrically coupled to sheet 144 such that at an RF frequency, sheet 142, sheet 144, and conformal shield 148 form an RF shield effective to shield RF signals from PET detector array 70 and the polarizing magnet 50 shown in FIG. 1.

Referring again to FIG. 5, according to one embodiment, sheets 142-146 are formed of a material such as a stainless steel mesh having an RF connectivity to allow for good or adequate RF shielding at RF frequencies yet having a high gradient impedance at gradient pulse frequencies. The use of this type of material (e.g., stainless steel mesh) in areas of high gradient coil dB/dt allows the RF shield to minimize or limit the generation of eddy currents therein when changes to the magnetic field are caused by the gradient coils. However, the use of conformal shields 148, 150 in the areas of RF shield 140 indicated herein allows for a reduction in manufacturing time and costs associated with the RF shield 140.

Conformal shields 148, 150 can have a higher susceptibility to eddy current generation than sheets 142-146 if they are applied and used in areas of low gradient coil dB/dt. Since the change in the magnetic field caused by the gradient coil is relatively low in these low gradient coil dB/dt areas, the use of a material that is more susceptible to eddy current generation than the material used for the areas of high gradient coil dB/dt might allow for the generation of more eddy currents, but since the change in the magnetic field is low, any eddy currents generated in the conformal shield will be much less than if the conformal shield were used in an area of high gradient coil dB/dt. Conversely, conformal shields 148, 150 made of a material having the same or similar susceptibility to eddy current generation as that of sheets 142-146 can be used and applied in areas at all levels of gradient coil dB/dt. In this manner, an RF shield having a substantially uniform susceptibility to eddy current generation can be constructed.

To assist in the reduction of a currents generated in conformal shields 148, 150, a slit or gap 152 may be formed in conformal shields 148, 150. For example, a separate slit 152 may be formed at each of a plurality of positions about conformal shield 148 about the circumference of former 82. FIG. 5 illustrates one such slit 152 formed in conformal shield 148 while the portion of conformal shield 150 shown in FIG. 5 is illustrated as lacking a slit 152. However, embodiments of the invention contemplate forming any number of slits 152 in either or both of conformal shields 148, 150 in multiple locations about RF shield 140. In addition, the slits 152 may be formed in equidistant positions about RF coil former 82. Similar to slits 108, slits 152 may be formed to have a width of 1 mm, for example, and are configured to reduce heating caused by gradient field induced eddy currents in the RF shield 84 during operation of the PET-MR imaging system 10 by increasing impedance for the gradient eddy currents due to increased path length.

Figure 7:
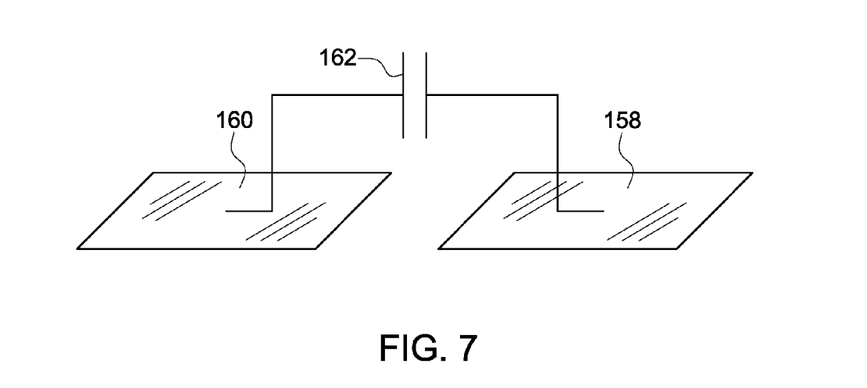
FIG. 7 is a schematic diagram showing electrical coupling of RF shield portions according to an embodiment of the invention.
Figure 8:
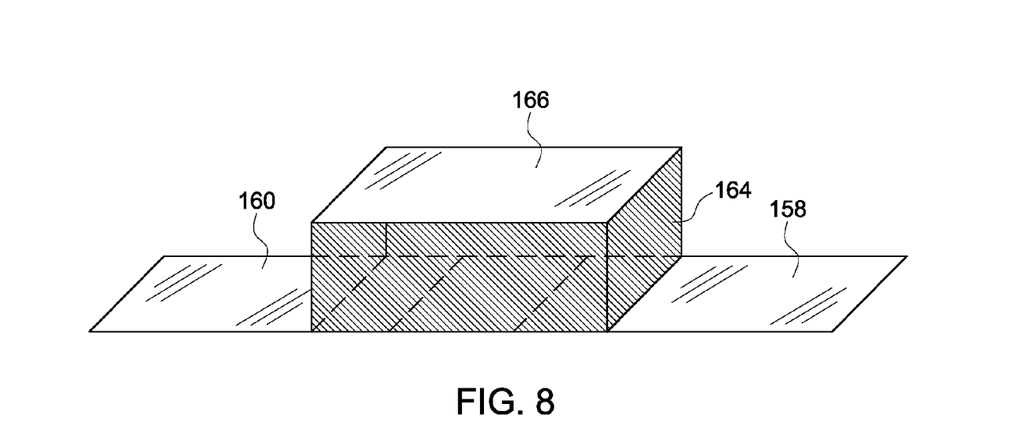
FIG. 8 is a schematic diagram showing electrical coupling of RF shield portions according to another embodiment of the invention.

A slit 154 adjoining slit 152 may be formed in sheet 142, and a corresponding slit 156 may be formed in sheet 142 to also adjoin slit 152. Slits 154, 156 increase the conductance path between separate portions 158, 160 of conformal shield 148. FIGS. 7 and 8 show alternative embodiments for coupling portions 158, 160 together at RF frequencies while leaving portions 158, 160 decoupled at gradient frequencies.

As shown in FIG. 7, a first embodiment for coupling portions 158, 160 together at RF frequencies includes coupling a capacitor 162 between portions 158, 160 such that the capacitance of capacitor 162 electrically shorts portion 158 to portion 160 at an RF frequencies while leaving the disconnection of portion 158 to portion 160 open at gradient pulse frequencies. The capacitor is thus configured to electrically couple portions 158, 160 together when an alternating voltage at an RF frequency is induced therein.

As illustrated in FIG. 8, a different manner of coupling portion 158 to portion 160 via capacitance is shown. In one embodiment, a dielectric material 164 is placed or positioned so as to overlap portions 158 and 160. An electrically conductive material 166 is then placed or positioned on the dielectric 164 such that capacitance is formed between material 166 and portion 158 and between material 166 and portion 160. Similar to the value of the capacitance of capacitor 162 of FIG. 7, the dielectric material 164 and electrically conductive material 166 as well as the spacing between electrically conductive material 166 and portions 158, 160 are chosen such that the value of the capacitance between material 166 and portions 158, 160 leads to an electrical short between portion 158 and portion 160 at RF frequencies and leads to an electrical open between portion 158 and portion 160 at gradient pulse frequencies. In one embodiment, material 166 comprises the same material as portion 158 and/or portion 160.

Beneficially, embodiments of the invention thus provide an RF shield for use in a PET-MR imaging system that is configured to accommodate positioning of the PET detector array. The RF shield includes an indentation formed therein that receives the detector array and provides for placement of the detector array outside of the RF shield to shield the sensitive detector array from the high amplitude RF fields of the MRI scanner and to prevent noise from the PET detector array to enter the MRI detector space. When formed as a conformal RF shield according to embodiments of the invention, manufacturing time and costs of the RF shield may be reduced.

Therefore, according to one embodiment of the invention, an imaging apparatus comprises a magnetic resonance imaging (MRI) system comprising a plurality of gradient coils positioned about a patient bore, an RF coil former comprising an inner surface and an outer surface, and a composite RF shield positioned adjacently to the outer surface of the RF coil former so as to be formed about the RF coil former. The MRI system also comprises an RF coil positioned on the inner surface of the RF coil former and about the patient bore, with the RF coil coupled to a pulse generator to emit an RF pulse sequence and receive resulting MR signals from a subject of interest. The RF coil former comprises a generally cylindrical member having an indented portion indented in a radial direction inwardly from the outer surface, and the composite RF shield comprises a first shield material positioned about the outer surface of the RF coil former, a second shield material position about the indented portion of the RF coil former, and a conformal shield material positioned about the RF coil former that electrically couples the first shield material to the second shield material.

According to another embodiment of the invention, a PET-MRI apparatus comprises a magnetic resonance imaging (MRI) system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest. The PET-MRI apparatus also comprises a positron emission tomography (PET) system having a detector array positioned to encircle the bore, with the detector array being controlled to acquire PET emissions of the subject of interest. The RF shield comprises a first RF shield portion forming a raised portion, a second RF shield portion forming an indented portion, the indented portion being indented from the raised portion in the radial direction inwardly toward the patient bore, and a conformal shield portion coupling the first RF shield portion to the second RF shield portion.

According to yet another embodiment of the invention, a method of forming a composite RF shield comprises positioning a first shield material about an outer surface of an RF coil former and positioning a second shield material about an indented portion of the RF coil former, wherein the indented portion indented in a radial direction inwardly from the outer surface. The method also comprises applying a conformal shield material about the RF coil former to electrically couple the first shield material to the second shield material.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging apparatus comprising:
a magnetic resonance imaging (MRI) system comprising:
 a plurality of gradient coils positioned about a patient bore;
 an RF coil former comprising an inner surface and an outer surface;
 a composite RF shield positioned adjacently to the outer surface of the RF coil former so as to be formed about the RF coil former; and
 an RF coil positioned on the inner surface of the RF coil former and about the patient bore, with the RF coil coupled to a pulse generator to emit an RF pulse sequence and receive resulting MR signals from a subject of interest;
wherein the RF coil former comprises a generally cylindrical member having an indented portion indented in a radial direction inwardly from the outer surface; and
wherein the composite RF shield comprises:
 a first shield material positioned about the outer surface of the RF coil former;
 a second shield material positioned about the indented portion of the RF coil former; and a conformal shield material positioned about the RF coil former, the conformal shield material electrically coupling the first shield material to the second shield material.

2. The imaging apparatus of claim 1 wherein the first shield material is coupled to the second shield material only through the conformal shield material.

3. The imaging apparatus of claim 1 wherein the first and second shield materials comprise a stainless steel mesh.

4. The imaging apparatus of claim 1 wherein the first and second shield materials comprise the same material.

5. The imaging apparatus of claim 4 wherein the conformal shield material comprises a material distinct from the material of the first and second shield materials.

6. The imaging apparatus of claim 5 wherein the material of the conformal shield material comprises one of copper and silver.

7. The imaging apparatus of claim 1 wherein the conformal shield material has a higher susceptibility to eddy current generation than the first and second shield materials.

8. The imaging apparatus of claim 1 wherein the conformal shield material comprises a plurality of portions spaced apart from one another via a slit.

9. The imaging apparatus of claim 8 further comprising a capacitor coupled between an adjacent portion pair of the plurality of portions, wherein the capacitor is configured to electrically couple the adjacent portion pair together when an alternating voltage at an RF frequency is induced therein.

10. The imaging apparatus of claim 9 further comprising:
a dielectric material positioned to overlap each conformal shield material portion across the slit; and
an electrically conductive material coupled to the dielectric material, the electrically conductive material forming a capacitance between each conformal shield material portion overlapping therewith.

11. A PET-MRI apparatus comprising:
a magnetic resonance imaging (MRI) system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest; and
a positron emission tomography (PET) system having a detector array positioned to encircle the bore, with the detector array being controlled to acquire PET emissions of the subject of interest;
wherein the RF shield comprises:
a first RF shield portion forming a raised portion;
a second RF shield portion forming an indented portion, the indented portion being indented from the raised portion in the radial direction inwardly toward the patient bore; and
a conformal shield portion coupling the first RF shield portion to the second RF shield portion.

12. The PET-MRI apparatus of claim 11 wherein the first and second RF shield portions comprise the same material; and
wherein the conformal shield portion comprises a material distinct from the material of the first and second RF shield portions.

13. The PET-MRI apparatus of claim 11 wherein the first and second RF shield portions are positioned in a non-overlapping arrangement.

14. The PET-MRI apparatus of claim 11 wherein the conformal shield portion comprises a spray-on conductive material.

15. The PET-MRI apparatus of claim 14 wherein the spray-on conductive material comprises one of an electrically conductive paint and an electrically conductive polymer.

16. A method of forming a composite RF shield comprising:
positioning a first shield material about an outer surface of an RF coil former;
positioning a second shield material about an indented portion of the RF coil former, the indented portion indented in a radial direction inwardly from the outer surface; and
applying a conformal shield material about the RF coil former to electrically couple the first shield material to the second shield material.

17. The method of claim 16 wherein applying the conformal shield material comprises spraying one of an electrically conductive paint and an electrically conductive polymer to overlap a portion of the first shield material and a portion of the second shield material.

18. The RF coil assembly of claim 17 wherein applying the conformal shield material comprises applying a conformal shield material having a higher susceptibility to eddy current generation in a changing magnetic field than a susceptibility of the first and second shield materials to eddy current generation in the changing magnetic field.

19. The RF coil assembly of claim 18 further comprising:
forming a gap in the conformal shield material to create a plurality of conformal shield portions; and
capacitively coupling the plurality of conformal shield portions together.

* * * * *